United States Patent [19]

Yoder, Jr.

[11] Patent Number: 4,993,826
[45] Date of Patent: Feb. 19, 1991

[54] TOPOGRAPHY MEASURING APPARATUS
[75] Inventor: Paul R. Yoder, Jr., Wilton, Conn.
[73] Assignee: Taunton Technologies, Inc., Monroe, Conn.
[21] Appl. No.: 344,368
[22] Filed: Apr. 28, 1989

Related U.S. Application Data
[63] Continuation-in-part of Ser. No. 125,240, Nov. 25, 1987, Pat. No. 4,902,123.
[51] Int. Cl.$^5$ ............................ A61B 3/10; A61B 3/00
[52] U.S. Cl. ...................................... 351/212; 351/247
[58] Field of Search ............... 351/205, 212, 247, 208; 356/124, 376

Primary Examiner—Rodney B. Bovernick
Attorney, Agent, or Firm—Kramer, Brufsky & Cifelli

[57] ABSTRACT

A contour measuring apparatus and method of using the same is disclosed to measure the three-dimensional contour of a surface. Structure is provided to direct first light beams onto the surface being measured. Reflections of the first light beams from the surface are received for generating electrical output signals corresponding to electro-optically measurable optical images. Each of the images corresponds to the location of the first light beams. Structure determines the approximate location of the center of the surface being measured with respect to an optical axis extending through the contour measuring apparatus. The location determining structure comprises a component for directing a single light beam along the optical axis of the contour measuring apparatus onto the surface being measured so as to reflect to the means for generating electrical output signals. Also, structure generates a pattern in the component for generating electrical output signals corresponding to the location of the optical axis to the contour measuring apparatus. Moreover, the apparatus includes an element to compare the location of the center of the surface being measured with the location of the optical axis.

42 Claims, 7 Drawing Sheets

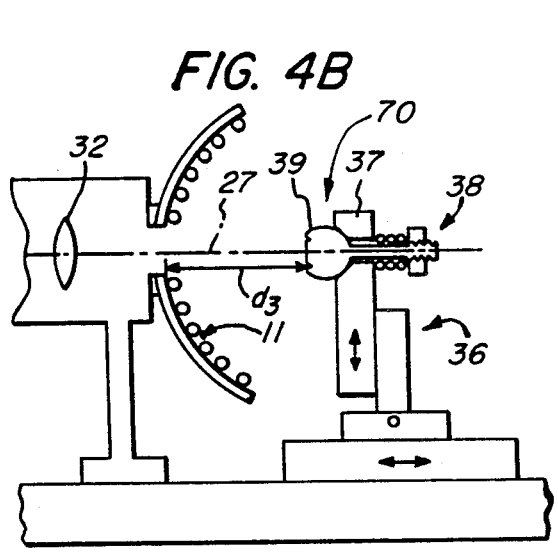
FIG. 4B
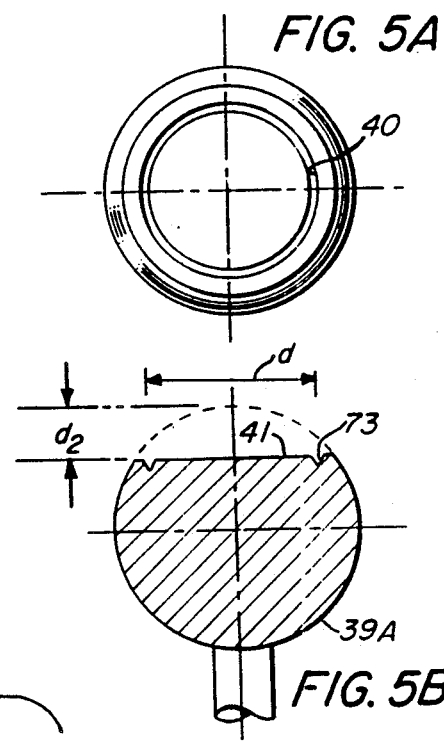
FIG. 5A
FIG. 5B
FIG. 5C
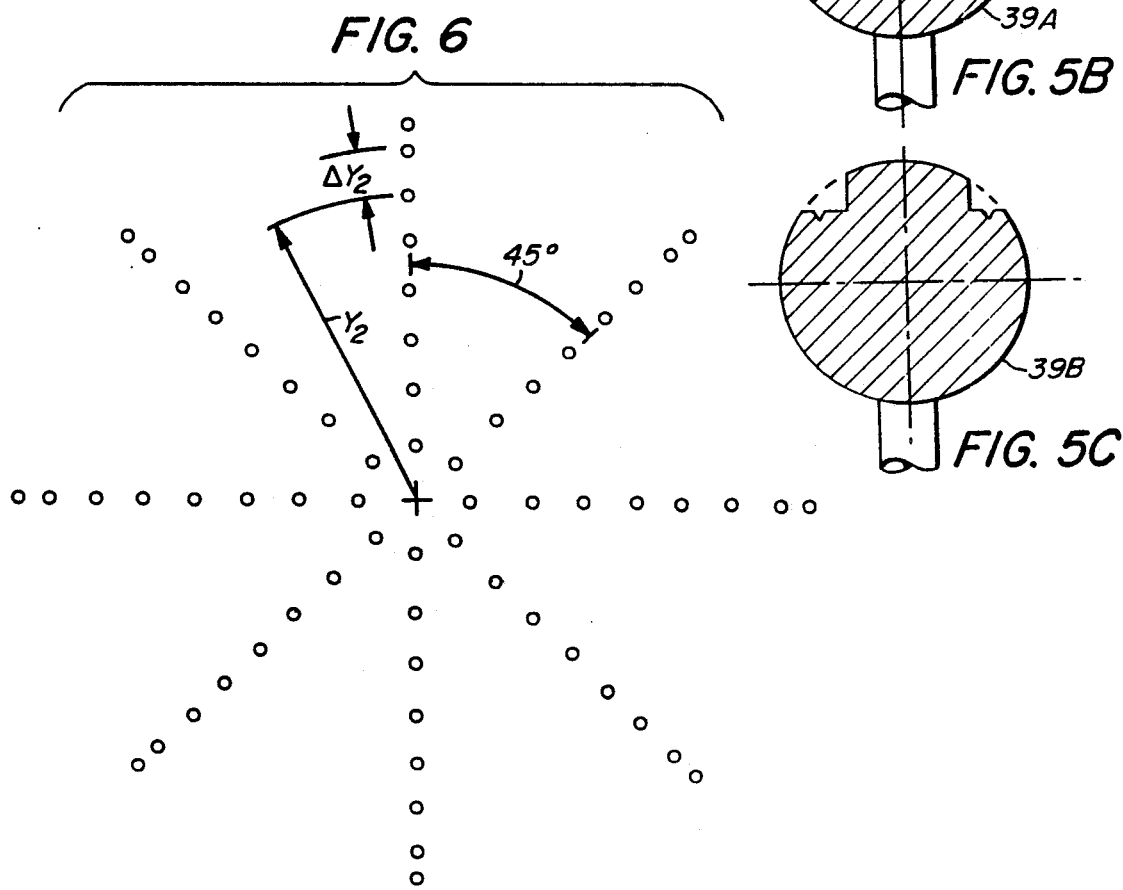
FIG. 6

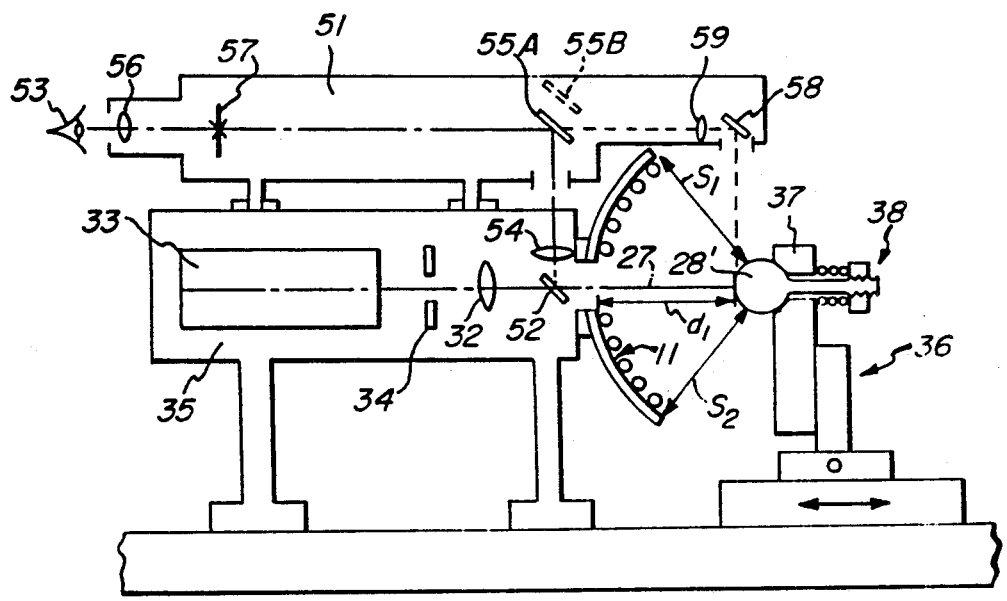
FIG. 9
FIG. 10
FIG. 11
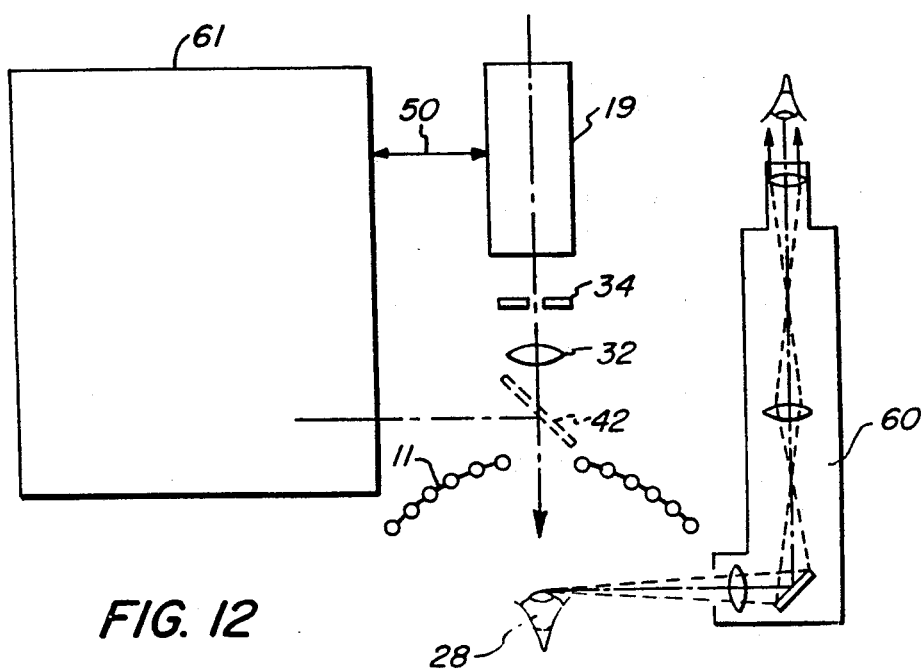
FIG. 12

TOPOGRAPHY MEASURING APPARATUS

This application is a continuation-in-part of U.S. patent application Ser. No. 125,240, filed Nov. 25, 1987, now U.S. Pat. No. 4,902,123.

BACKGROUND OF THE INVENTION

While the invention is subject to a wide range of applications, it is particularly suited to measure the three-dimensional contour of a surface. In particular, this invention relates to that aspect of ophthalmic diagnosis which is concerned with measurement of the three-dimensional contour of the anterior surface of the cornea. This measurement discloses abnormalities in the cornea which may have deleterious effects upon vision or quantifies progress of ophthalmic surgery, such as laser-aided radial keratotomy or laser ablation of the external surface of the cornea with penetration into the stroma and volumetric removal of tissue, whereby the external corneal surface is characterized by a sculptured, new curvature having improved optical properties.

Devices variously called corneascopes or keratometers have been developed for topographic analysis of the cornea. Such devices have found acceptance as means for measuring corneal curvature in preparation for prescribing a contact lens to be worn over the measured cornea to reduce certain visual defects, or for use in other ophthalmic applications. The prior art for these devices entails photographic (as in U.S. Pat. No. 3,797,921, Kilmer, et al.) or electro-optical (see U.S. Pat. No. 4,572,628, Nohda) recording of cornea-reflected images of illuminated objects comprising several concentric rings, or multiple discrete light sources arranged in the form of concentric rings, on a flat surface normal to the optical system axis or on a concave surface symmetrically disposed with respect to that axis. If the cornea is spherical, the reflected images of these ring-shaped objects are equally spaced, continuous or intermittent, concentric ring-shaped patterns. If the cornea surface is rotationally symmetrical but not spherical, the resultant ring images are less equally spaced; the inequality of spacing is thus a measure of nonsphericity of the cornea surface. If the cornea surface is astigmatic, as is frequently the case, the ring-shaped images reflected by that cornea will appear elliptical, and the eccentricity of the pattern is related to the change in curvature of the cornea surface between various sectional meridians. This eccentricity, and hence the astigmatism of the surface, can be measured by careful analysis of an image of the ring pattern. The orientation of the major and minor axes of the elliptical pattern relative to the eye indicates the orientation of the principal axes of the observed astigmatism. If the cornea has been warped or distorted by injury, by disease or by prior surgical procedures, such as radial keratotomy or imperfect closure of incisions made during cataract or other surgery, the magnitudes of these surface defects can also be measured.

In each of these described cases, the desired end result is (1) a tabular or graphic representation of the surface optical power (in units of diopters) at various points over the visually used, central portion of the cornea (typically 3 to 7 mm in diameter), and (2) computed average values for these parameters over the area of interest. Because of the tendency for the eye to become astigmatic, or non-rotationally symmetrical, comparisons of surface radius or power are frequently made for various azimuthal meridians about the visual axis. Instrument errors introduced by the apparatus and systematic or random errors introduced by the method of use are preferably minimized in order to minimize the overall measurement error. Prior art devices for accomplishing these measurements have been found lacking in regard to one or more of the following attributes: accuracy, ease of use, and time required to obtain the desired tabular or graphical output. None of these devices is compatible with use in situ and in close temporal alignment with surgical laser sculpturing of the cornea to produce desired net curvature changes to improve vision.

BRIEF STATEMENT OF THE INVENTION

It is an object of the invention to provide a method and means for improving the accuracy and speed with which the topography of the anterior surface of the cornea can be measured.

It is a specific object to meet the above object by incorporating a self-calibration capability which ensures that the instrument error of the measurement is small.

It is another object to incorporate a simple means for achieving proper location and orientation of the eye under test with respect to the diagnostic apparatus.

A further specific object is to make possible the measurement of corneal radius, and thus optical power, at individual small, localized areas on the surface.

Another object is to provide an in situ means for observing the exterior of the eye and for measuring the topography of the cornea surface at selected times before, during and after performance of surgical procedures such as are taught by L'Esperance, Jr. U.S. Pat. No. 4,665,913, No. 4,669,466, No. 4,732,148 and pending U.S. Ser. No. 891,169. Those applications cover the ablation of the cornea with penetration into the stroma and volumetric removal of corneal tissue through controlled application of radiation from an ultraviolet laser, or similar procedures utilizing radiation of longer wavelength such as an infrared laser operating at about 2.9 micrometers.

It is a still further object of the present invention to enhance the accuracy and repeatability of the measurement of the corneal radius.

It is yet another object of the present invention to provide apparatus which aids in the centering of a patient's cornea with respect to the diagnostic apparatus.

The invention achieves the foregoing objects by analyzing the pattern of images of an array of light points specularly reflected from the surface being measured such as the convex surface formed by a cornea being measured for diagnostic purposes or, for example, a spherical ball of known radius of curvature used for apparatus calibration purposes. In a preferred embodiment, the apparatus is capable of interfacing directly with apparatus as described by Telfair, et al., in pending patent applications Ser. No. 938,633 now U.S. Pat. No. 4,911,711 and Ser. No. 009,724, now abandoned so as to permit diagnostic evaluation of a given cornea in conjunction with surgical sculpturing of the same cornea with laser radiation to improve its optical properties.

In a second embodiment, the apparatus is capable of employing an added dimension of information to realize higher spatial resolution without having to deal with the spacing of the array of light points which is too small to accurately resolve.

A third embodiment of the present invention includes an apparatus to achieve centering alignment of the eye in the transverse directions with high accuracy as well as the ability to provide information about the corneal topography very close to the optical axis through the keratoscope of the present invention.

BRIEF DESCRIPTION OF THE DRAWINGS

The invention will be illustratively described for preferred and other embodiments, in conjunction with the accompanying drawings, in which:

FIG. 4B is a similar but fragmentary diagram to illustrate a modification;

FIGS. 5A and 5B are respectively front-end and longitudinal-section views, to an enlarged scale, for a calibration element in FIG. 4B, and FIG. 5C is a modified calibration element.

FIG. 6 is a representation, in a radial-plane projection, for an illustrative distribution of multiple light sources in the array of FIG. 2;

FIG. 9 is a further development of FIG. 4A incorporating means to measure alignment of the eye calibration device relative to the diagnostic apparatus;

FIG. 10 shows the typical appearance of the visual field of the focus alignment sensing means in the calibration mode;

FIG. 11 shows the typical appearance of the visual field of the focus alignment sensing means in the operational mode;

FIG. 12 is a simplified diagram relating the focus alignment sensing means to a laser sculpturing apparatus;

DETAILED DESCRIPTION OF THE INVENTION

Figure 1:
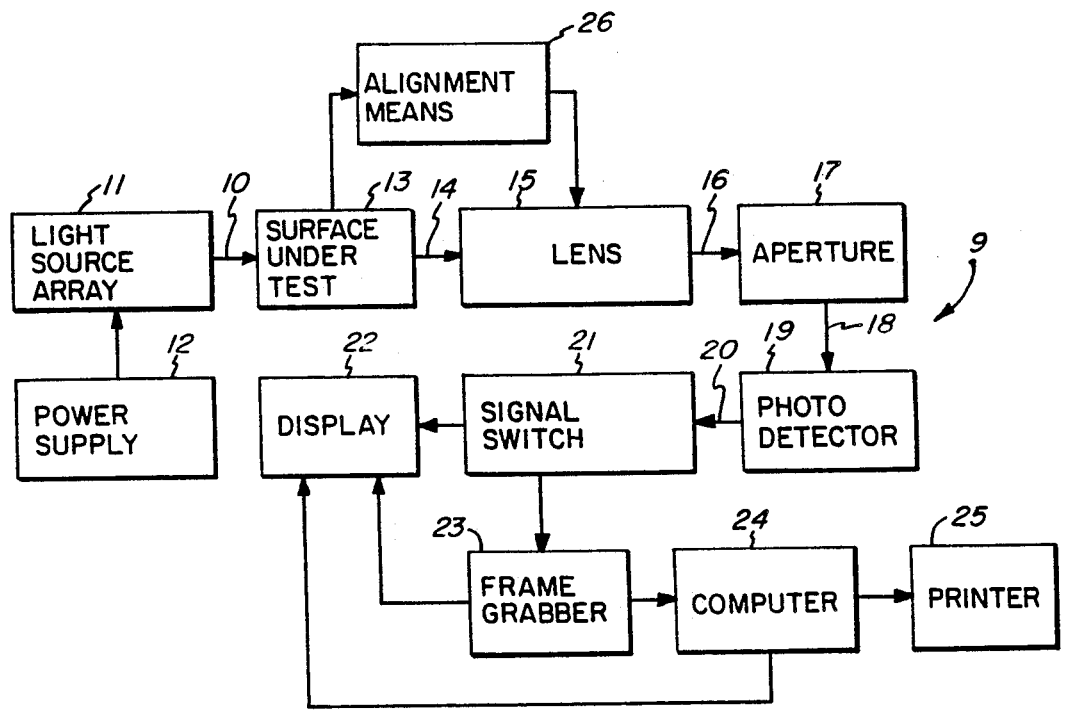
FIG. 1 is a simplified block diagram to show the functional relationships of generalized optical, mechanical and electrical components of topography-measuring apparatus of the invention.

A contour measuring apparatus 9 to measure the three-dimensional contour of a surface 13 is disclosed. The apparatus 9 includes a multi-point light source 11 to direct a plurality of individual light beams 10 onto the surface 13. A photodetector 19 produces electro-optically measurable optical images. A lens 15 is disposed between the surface 13 and the photodetector 19 to focus the reflected beams of light 14 from the surface being measured 13 onto the photodetector 19 to form the measurable optical images. A signal switch 21, a frame grabber 23, and computer means 24 are in electrical communication with said photo-detector 19 for determining both the local radius of curvature of the surface 13 at each desired point of incidence of the individual light beams and the three-dimensional contours of the surface 13. A calibration device 70 is provided to reduce instrument errors of the apparatus 9. The calibration device 70 includes a calibration surface 72 with a known contour to be positioned in substitution of the surface 13 being measured. Components 21 and 23 sequentially determine and store in memory the location on said calibration surface 71 of each image of individual light points. Means 24 further determine the contour of the surface 13 being measured from a differential evaluation of the reflection of each light point image from the surface 13 being measured in comparison to the reflection of each light point image from the calibration surface 71 with a known contour.

In FIG. 1, the invention is shown as an apparatus 9 for producing and interpreting images reflected from a surface under test. An array 11 of light sources is activated by a power supply 12, and multiple diverging light beams 10 from the array are intercepted by a contoured surface 13 under test; contoured surface 13 acts as a mirror to reflect light beams 14 into a lens 15 which, in turn, focuses those light beams 16 through an aperture or iris 17. The beams 18 emerging from aperture 17 are then focused onto the sensitive surface of a photodetecting means 19. Electrical output signals 20 generated by means 19 are directed by a signal switch 21 to a frame grabber 23 which produces a time-sequenced series of electrical signals representative of the spatial distribution of energy in the image formed by lens 15. These electrical signals can be displayed as a real time video image in a display apparatus 22. Alternatively or in addition, the electrical signals can be stored in digital form by a frame grabber 23, for further analysis by a computer 24 and/or for supply to display means 22 or print-out means 25. Special algorithms stored in computer 24 permit computation of the radius of curvature, and hence of the optical power, of contoured surface 13 at the point of incidence on said surface of the beam from any one light source in the array 11. Means 26 allows the optical alignment of the surface 13 relative to the axis of lens 15 to be measured.

Figure 2:
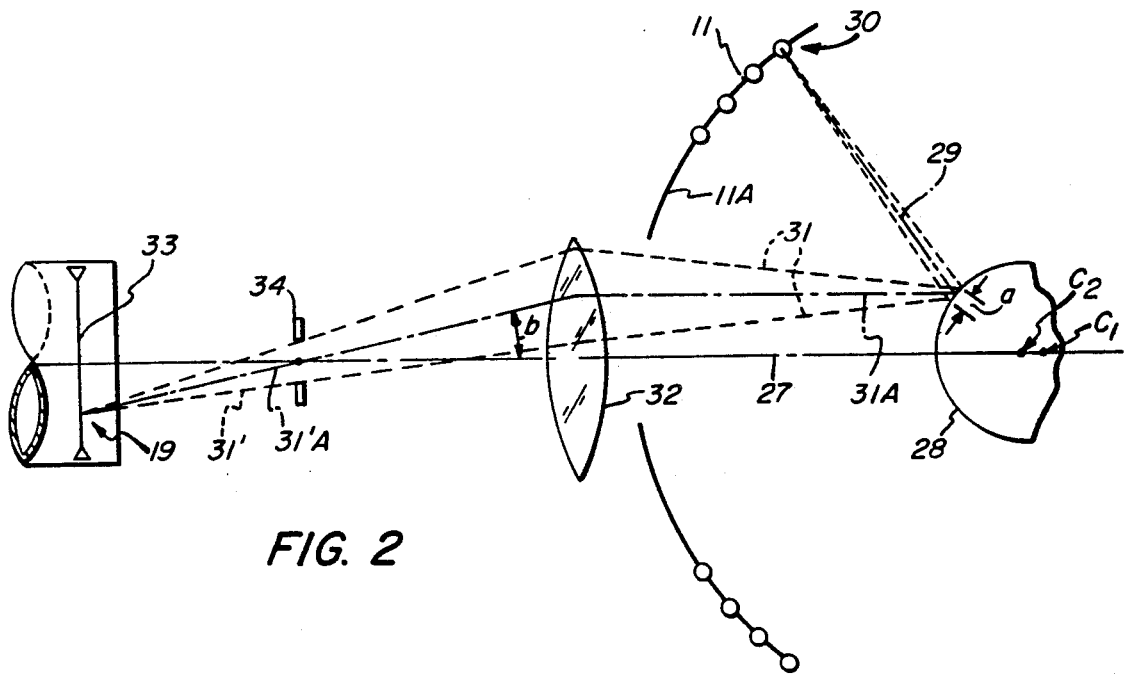
FIG. 2 is a diagram of principal optical components of FIG. 1, including an array of multiple light sources.

Further detail as to function of the involved optical system of the invention is shown in FIG. 2, wherein the array 11 comprises a plurality of individual light emitting diodes (LEDS) disposed on a nominally spherical surface 11A, of known contour, having its center $C_1$ on the optical axis 27 of the system. Preferably, the surface 11A is nominally spherical; however, it is within the terms of the invention for the surface 11A to be of any desired shape. Although the array 11 of light sources preferably is comprised of LEDs, it is also within the terms of the present invention to construct the array 11 of any type of light sources, such as a plurality of fiber optics. The center $C_2$ of a convex surface 28, equivalent to surface 13 in FIG. 1, under test also lies on the axis 27 but does not necessarily coincide with $C_1$. One of the beams 10 is the divergent beam 29 from a typical LED 30 which is redirected, upon reflection from surface 28, as a more divergent beam 31 of the beams 14 into the aperture of a lens 32. The lens 32 is preferably centered on axis 27 and located at an appropriate distance downstream from surface 28. Through the image-forming properties of lens 32, an image of the typical LED 30 is produced at some point on the photocathode 33 of a conventional photo-detecting device 19 which may be a vidicon-type image tube; alternatively, device 19 may be an array of discrete detectors such as a charge coupled device (CCD). Typically, the photocathode of such an image tube or array would have usable aperture dimensions of about 6.6×8.8 mm and would be sensitive to the visible light emitted by the light source 11. Because of the inherent rotational symmetry of the various optical and electro-optical components about the axis 27, the image of the entire array 11 typically lies within a circle inscribed within the rectangular usable aperture of the photocathode. It should be noted that the photodetector means 19 is in no way limited to the indicated light source or particular dimensions, in that larger or smaller devices of like or different nature may be accommodated by selection of the specific type of photodetector 19 and by appropriately scaling the size of the image.

A feature of the invention is the inclusion of an aperture such as iris 34 located on the axis 27, offset from lens 32 at a distance substantially equal to the back focal length (BFL) of the lens 32, thus placing iris 34 at the focal point of the lens. The opening of iris 34 is constrained to always be small enough that it, rather than the aperture of lens 32, determines the angular size of the conical beam 31' of beam 18. The iris 34 acts as the aperture stop of the system and controls the cone angle of the individual beams 14, 16, 18, 31', 31 and 29 as well as the size of the area "a" on test surface 28 which contributes light from the typical LED 30 to the corresponding image point on photodetecting means 19. Since iris 34 is located at the focal point of lens 32, light rays 31'A passing centrally through the iris, at any angle "b" with respect to axis 27, must propagate parallel to axis 27 in the space between test surface 28 and lens 32. These rays 31'A, called principal rays, are then said to be telecentric in the object space of lens 32, and the aperture stop 34, i.e., the iris, is a telecentric stop. The opening in the iris 34 can be small since the LEDs are intrinsically very bright and the image sensor is very sensitive to incident light. All the rays in the beam from a given LED are therefore physically near each other and all closely approximate the path of the appropriate principal ray.

The fact that the principal rays from all LEDs in the array 11 travel parallel to axis 27, after reflecting from surface 28, allows use of a simple mathematical process to independently compute the average radius of surface 28 over each of the small localized areas of dimension "a" centered about the intercept points of the principal rays on surface 28.

Figure 3:
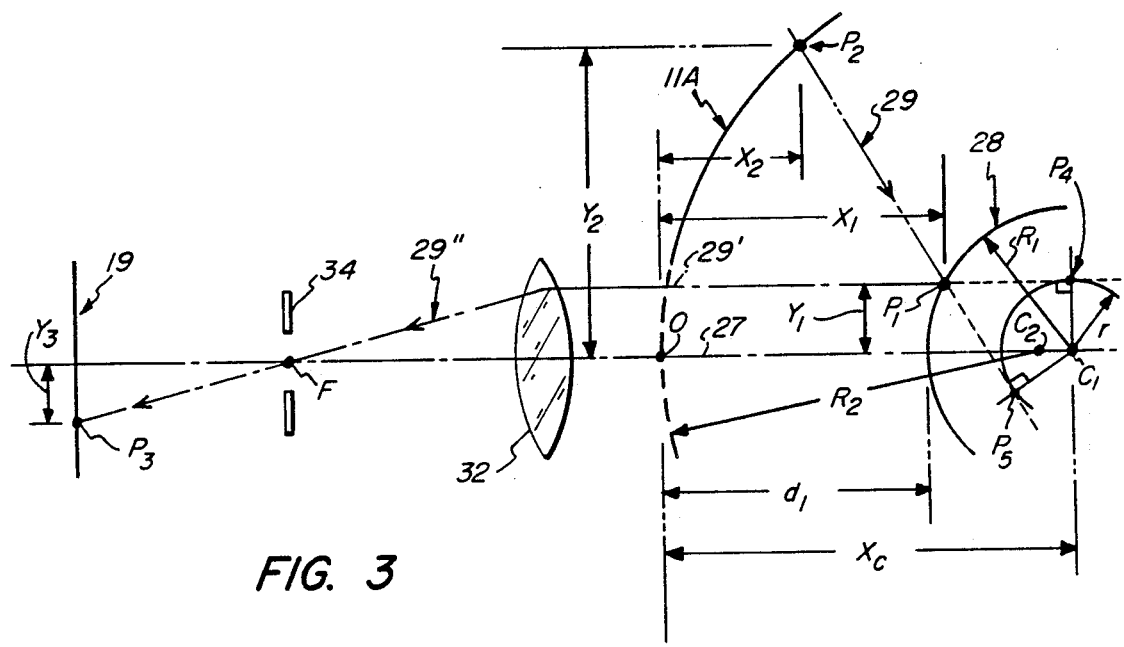
FIG. 3 is a diagram showing certain geometric relationships that are pertinent to the optical arrangement of FIG. 2.

FIG. 3 illustrates the applicable geometrical condition. It may be noted that surface 28 is located at an axial distance $d_1$ from surface 11A and that the principal ray 29 from a typical LED 30 (here assumed to be a point source of light at $P_2$) intercepts surface 28 at a height $Y_1$ from the axis 27 and proceeds to lens 32 as ray 29' parallel to said axis. Ray 29' becomes ray 29" beyond lens 32 and passes through focal point F in route to point $P_3$ at the image plane within the image sensor 19. The radial distance $Y_3$ of $P_3$ from the axis 27 is related to $Y_1$ by the lateral magnification ratio inherent in the lens 32. A method for determining this magnification ratio is described later in this description.

The law of reflection at an optical surface requires the path of ray 29 from $P_2$ to $P_1$ to be such that (a) its extension (dashed line) through surface 28 and (b) the extension (dashed line) of reflected ray 29' are both tangent (at $P_5$ and $P_4$· respectively) to a circle constructed concentric with surface 28. The perpendicular distance from tangent point $P_4$ to center $C_1$ thus equals the perpendicular distance from tangent point $P_5$ to that same center. For convenience, both of these distances will be referred to as "r", which may be expressed:

$$r = \frac{A X_c + B Y_c + C}{\sqrt{A^2 + B^2}} ; \qquad (1)$$

where:

$A = Y_1 - Y_{2'}$ $B = X_2 - X_{1'}$ and $C = X_2 Y_1 - X_1 Y_2$ and $X_{c'}$, $Y_c$ are the coordinates of center $C_1$ measured from X and Y axes through origin "0" at surface 11A. Since ray 29' is parallel to axis 27, as shown in FIG. 3, r also equals $Y_1$. In the nominal case, $Y_c = 0$, since $C_1$ lies on the X axis.

As mentioned in connection with FIG. 1, the image on the photodetector 19 can be analyzed mathematically. A frame of multiple LED images can be stored digitally by frame grabber 23 for subsequent analysis in computer 24 and display at 22. The results of the analysis can be tabulated and various representations of the surface contour printed by printer 25. The information needed to compute the radius of curvature of the surface 28 at various points comprises the radial distance $Y_3$ for each of the images of the LEDs in array 11. Since the magnification ratio of lens 32 can be determined, the corresponding heights $Y_1$ can be computed.

When the coordinates of $P_2$ and of $C_1$ and the Y coordinate of $P_1$ are known, the unique value of $X_1$ can be computed from the quadratic equation:

$$X_1 = \frac{-E \pm \sqrt{E^2 - 4DG}}{2D} ; \qquad (2)$$

where:

$D = A(2Y_1 - A)$, $E = 2A(AX_c - X_c Y_1 - X_2 Y_1)$, and $G = A^2(Y_1^2 - X_c^2) + 2AX_c X_2 Y_1$ Once $X_1$ and $Y_1$ are known, the radius $R_1$ at $P_1$ can be computed from the expression:

$$R_1 = \sqrt{Y_1^2 + X_1^2} \qquad (3)$$

In general, the axial distance $d_1$ between the surfaces 11A and 28 can be measured by standard means. Hence, $$X_c = d_1 + R_1 \qquad (4)$$

Since radius $R_1$ is initially unknown, an iterative procedure may be used wherein a reasonable value for $R_1$ is chosen and substituted into Equation 4 to give a first approximation for $X_c$. Then, values of the coefficients A, D, E and G are determined, and a first approximation value for $R_1$ is computed from Equation 3. Successive computations give progressively more precise values for $R_1$; the iterative process is stopped when the desired precision is achieved.

This mathematical process is repeated for each LED image, and the local radius of the cornea is computed, for each of the various locations intercepted by narrow beams from the individual LEDs. The average radius of the surface, the extreme long and short radii of said surface, the dioptric equivalent of each of these radii, and the difference in average optical powers in the directions of the principal astigmatic meridians, as well as the azimuthal orientations of said meridians, can then be determined using methods of analytic geometry.

Figure 4A:
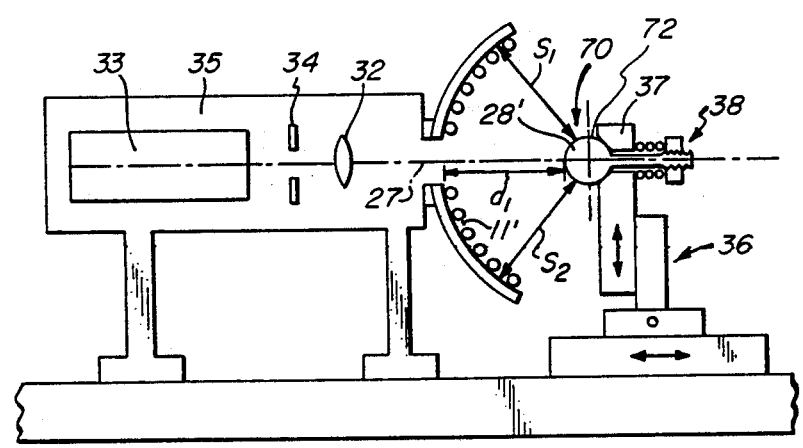
FIG. 4A is a simplified optical diagram of apparatus of FIG. 1, arranged in a calibrating mode.

The location for each luminous point $P_2$ must be known in order for the last described computational process to be used. These locations can be determined by directly measuring the coordinates of each LED source of the array 11. Alternatively, and preferably, this location can be determined with a calibration device 70. The calibration device includes a surface 71 of known contour. This surface 71 may comprise a spherical surface. A preferred technique of performing the calibration of apparatus 35 is accomplished by inserting a substantially spherical member 72 having a spherical surface 28' of precisely known radius into the apparatus 36. The spherical member 72 is located with its center on axis 27 at distance $d_1$ from surface 11A, as shown in FIG. 4A. The spherical member 72 can be positioned in the axial direction and in two transverse directions with respect to topography measuring apparatus 35, using adjusting means 36 which may typically comprise a three-dimensional translation stage. Proper centering is indicated by equality of the dimensions $S_1$ and $S_2$ to each other in the plane of FIG. 4A, as well as in the plane which includes axis 27 and is perpendicular to FIG. 4A. Adjustments to locate surface 28' at the specified distance $d_1$ from the spherical LED locus (surface 11) can be accomplished by the linear adjustment means of fixture 36. Once initially aligned, a conical seat 37 and a spring-loaded clamping means 38 provide a convenient and reliable means for relocating the spherical member 72 at its prescribed location, whenever calibration is to be rechecked.

In order to use the reflecting spherical member 72 as a calibration means, or to use the corneascope-type apparatus 35 to determine the topography of a cornea under test, the magnification of lens 32 must be known. This parameter can be measured as indicated in FIG. 4B, where a fiducial target member 39 is inserted in the adjustable fixture means 36 against the seat 37 at an axial distance $d_3$ from surface 11A. Then, a determination is made of the size of the corresponding image of the surface of target 39 on photodetecting means 19. The ratio of the measured image dimension to the actual object dimension is the magnification of the optical system, or lens 32. Typically, the absolute value of said magnification is about 0.4 to 0.6 times.

The ideal value of $d_3$ is slightly greater than $d_1$ since target surface 41 should be located essentially at the same distance from lens 32 as the image of the LEDs reflected by convex surface 28. The latter image is virtual and located at a distance behind said surface 28 given by the expression:

$$d_2 = (R_1 d_1)/(2d_1 + R_1) \tag{5}$$

Typically, for $d_1 = 100$ mm and $R_1 = 8$ mm, $d_2 = 4.2$ mm and $d_3 = d_1 + d_2 = 104.2$ mm. This location of the fiducial target surface 41 ensures that the images at the photodetector 19 of the LEDs and of the fiducial target will both be in focus.

By virtue of the telecentric nature of the optical system in object space of the lens 32, the magnification is essentially constant for moderate variations (of the order of a few millimeters) in the distance $d_1$. Since the location of a given point on the photosensitive surface of photodetecting means 19 is generally derived by measuring the distance of the point in units of pixel (picture element) widths horizontally and pixel heights vertically from some reference (such as a corner of the rectangular raster), and since the dimensions of a typical pixel may be different in these directions, the linear magnifications in these two directions may differ from each other. The measured values would generally be stored in computer memory for use at appropriate times during the subsequent computations.

The fiducial target 39 may be any of a variety of types such as two or more separated marks 73 so designed as to reflect or absorb light thereby becoming visible due to contrast against the background formed by the underlying surface of the target substrate. Since magnification can vary azimuthally about the axis 27 of an optical system, it is advisable to have dual fiducial marks on each of at least two mutually perpendicular intersecting diameters. In a preferred simple embodiment, a circular fiducial ring 40 is scribed or otherwise marked on the fiducial target substrate 39. The ring 40 is then located so as to be concentric with the axis 27, as indicated in FIGS. 5A and 5B. The fiducial ring 40 may be generated on a flattened surface 41 of an otherwise spherical target body 72, e.g., a flat locally ground on a tooling or bearing ball. It can then easily be seated against the conical seat 37 of the adjusting means 36 of FIG. 4B, thereby assuring proper centering with respect to the spherical LED locus 11 and to the axis 27. The depth of material removed in generating the flattened surface of the fiducial target on a sphere of radius $R_1$ is equal to the aforementioned dimension $d_2$.

As indicated in FIG. 5C, the functions of the spherical reflecting calibration surface 28' and of the fiducial target 39 can be combined as at 39B by suitably machining a spherical ball.

In a calibrating use, the LED sources are illuminated and the corresponding locations of the images at the image sensor 19 determined in the same manner as for the corneal reflections previously described. After converting these images to corresponding heights $Y_1$, the actual X and Y coordinates of the points $P_2$ for all the LEDs can be computed. This is the self-calibration process referred to as one object of the invention.

The method for accomplishing this computation also relies upon the law of reflection at surface 28 and mathematical expressions derived from analytic geometry, as follows:

$$Y_2^4 + IY_2^3 + JY_2^2 + LY_2 + M = 0; \tag{6}$$

where:

$$H = 4K_2^2 + K_3^2$$

$$I = (4K_2K_3R_2 + 2K_3K_4 + 8K_1K_2)/H$$

$$J = (4K_1^2 + 4K_1K_3R_2 + 4K_2K_4R_2 + 2K_3K_5 + K_4^2)/H$$

$$L = (4K_1K_4R_2 + 4K_2K_5R_2 + 2K_4K_5)/H$$

$$M = (4K_1K_5R_2 + K_5^2)/H$$

$$K_1 = (X_c - X_1)Y_1^2$$

$$K_2 = (X_1 - X_c)Y_1$$

$$K_3 = Y_1^2 - X_c^2 + 2X_cX_1 - X_1^2$$

$$K_4 = 2(X_c^2Y_1 - X_cX_1Y_1 - Y_1^3)$$

$$K_5 = Y_1^4 + X_1^2Y_1^2 - X_c^2Y_1^2$$

Once the $Y_2$ values have been computed it is a simple matter to compute the corresponding $X_2$ values from the expression:

$$X_2 = \sqrt{R_2^2 - Y_2^2} \tag{7}$$

where $R_2$ is the known radius of curvature of the spherical locus of all the LED sources (i.e., points $P_2$).

This feature of the present invention allows the corneascope to be calibrated thereby negating the deleterious effects of unavoidable manufacturing uncertainties in locations of the LED light sources used in calculating the corneal radius. By accomplishing this calibration periodically, instrument errors can be reduced to a minimum, and the resultant precision in measuring radius of curvature and dioptric power at a given point on the cornea is improved significantly over that achieved with prior art methods and apparatus.

In order to provide radius information at an adequate number of points over the circular area of interest on the cornea (typically of 5 to 7 millimeters diameter, centered on the optical axis of the eye) for ophthalmic diagnosis purposes, the light-source array 11 preferably includes many individual point light sources. FIG. 6 illustrates such an array comprising 64 LEDs arranged as 4 rows of 16 LEDs each crossing the aperture of the array, along meridians oriented at 45-degree intervals of azimuthal angle. The LEDs are located on a concave spherical surface to minimize the overall size of the apparatus while providing the required angular inclination of narrow beams from the individual sources to the subsequent optical elements in the system. It will be understood that additional light sources can be included along each meridian in the array, or additional meridians can be added in total or in part, if more information about the corneal contour is needed; conversely, fewer light sources may be used if less information is needed. In an alternate embodiment, a full complement of many light sources could be installed, but specific geometric groupings of sources could be selected by a suitable switching arrangement (not shown) to fit the need of a particular measurement to be accomplished at any time, thereby reducing the overall time required for processing and analysis of the data.

As was pointed out earlier in this description, the physical aperture diameter of the telecentric stop (iris) 34 can be quite small and yet allow sufficient light to pass through the system to produce detectable images on the photosensing means 19. Calculations pertinent to a particular embodiment of the invention indicate that, for image quality reasons, the image-forming beam should have an effective relative aperture no larger (i.e., no faster) than f/13. This has a secondary effect upon the performance of the image-forming system in that it significantly increases the depth of field for the LEDs and allows sharp images thereof to be formed at all points within the field of view. Some prior art systems used for this purpose have exhibited degraded image sharpness at edges of their field of view due to uncorrected aberrations related to the large effective relative aperture used therein.

The radial distance $Y_2$ indicated for a typical LED in FIG. 6 corresponds to the Y coordinate of point $P_2$ in FIG. 3, and it will be noted that radial separations $\Delta Y_2$) between LEDs along any meridian are not constant. This circumstance reflects the preferred condition of equal radial separations $\Delta Y_1$) of adjacent incidence points $P_1$ for the principal rays on surface 28. If the surface 28 is spherical, the corresponding radial separations of image points in the image plane at photo-detecting means 19 also are equal. While not essential to the function of the apparatus, this equality of image spacing facilitates detection of surface 28 irregularities, including astigmatism, when the composite image of the entire LED array is observed on the display 22 of FIG. 1 or is shown in hard copy produced by printer 25.

Figure 7:
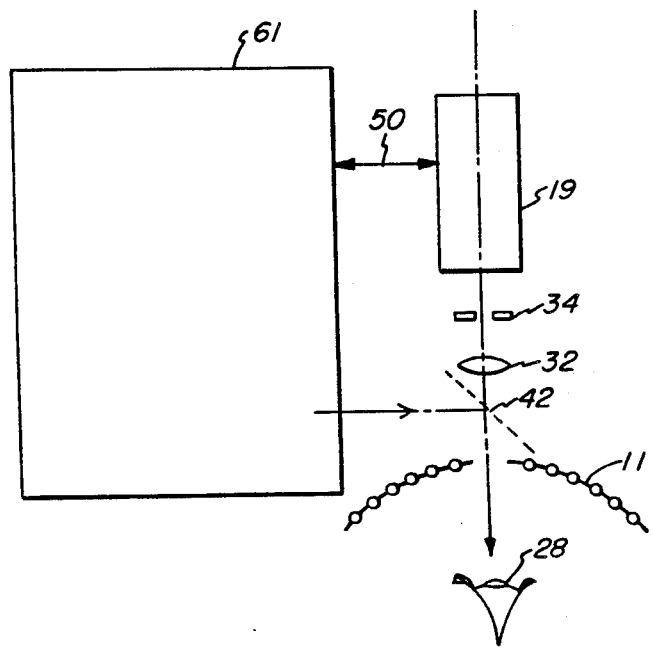
FIG. 7 is a diagram to illustrate use of the invention in conjunction with apparatus for surgical sculpture of the cornea.

In FIG. 7, the invention is shown in simplified form, interfacing directly (via a fold mirror 42) with laser-sculpturing apparatus 61 of the general type described by Telfair, et al., in patent applications Ser. No. 938,633 and Serial No. 009,724. When the fold mirror 42 is removed from the beam, the present corneascope-type topography measuring device can be used to evaluate the contour of the cornea 28 located near the center of curvature of the array 11. If a beamsplitter is used in lieu of the mirror 42, the diagnostic function can be accomplished in near-real time with laser sculpturing. In either of these events, a synchronizing connection 50 is shown between the sculpturing apparatus 61 and the photosensitive device 19 of the topography measuring apparatus, to assure at least an interlaced separation of sculpturing versus measuring functions in the course of a given surgical procedure.

Inasmuch as the image formed by lens 32 on photodetecting means 19 is not limited to the specific 5 to 7 millimeter diameter area of interest in diagnostic evaluation of the topography of the cornea, the described apparatus can be used to observe a large portion of the exterior of the eye under magnification, as in a surgical microscope.

Figure 8:
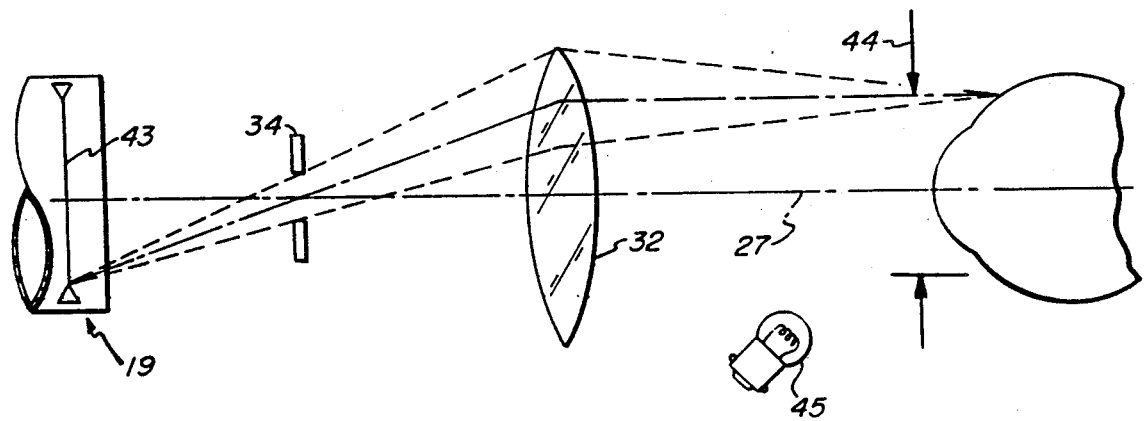
FIG. 8 is an optical diagram to show another application of the invention.

As depicted in FIG. 8, the field of view of the optical system is determined by the angular subtense of the sensitive area 43 on photodetector 19, as measured from the center of the aperture stop 34. Typically, the extent 44 of said field of view at the eye under examination is 12 to 16 millimeters in diameter, depending upon the specific combination of parameters in the design.

The image of the eye is presented in real time to the observing ophthalmologist and to other interested parties via the video subsystem comprising the vidicon or CCD array 19, signal switch 21 and display 22. Illumination of the eye is provided by a light source 45 which will be understood to be a single lamp or a multiplicity of lamps, e.g., room lights. By use of appropriate video components, the display can be presented in monochrome (i.e., black and white) or in true or false color.

Inherent in successful functioning of the invention is establishment of the proper axial distance $d_1$ (see FIG. 3) between the light source 11 and the surface under test 28. Mathematical analysis clearly shows that, in order to achieve $\pm \frac{1}{4}$ diopter precision in corneal refractive power measurements, the dimension $d_1$ must be held constant within approximately ±0.25 mm of the design value during calibration and operation.

This level of distance measurement and control can be achieved in a variety of ways. For example, a simple mechanical probe of calibrated length can be extended from the topography measuring apparatus to just touch the surface 28 at its axial vertex when said surface is at the proper location. The possibility of damaging the test surface with a probe precludes its application to ophthalmic applications. Non-contacting (optical or electro-optical) means such as ones functioning in a rangefinding mode in cameras to establish focus or means using inclined projected light beams which superimpose when incident upon the test surface if said surface is located at the proper (precalibrated) axial distance or means which illuminate a multi-element detector array by reflected specular or scattered light can typically be applied here.

A simple, preferred, non-contacting means for focus sensing employs an optical microscope (commonly called a "telemicroscope") with a long working distance, i.e. the clearance between object observed and the nearest surface of the microscope, so oriented as to allow the surface 28 to be seen in profile from a direction normal to the optical axis of the topography measuring apparatus. By attaching this telemicroscope to the topography measuring apparatus in stable fashion, so its line of sight does not change location with time, it can be utilized as a fixed reference for focus distance measurement. The telemicroscope can also be used to establish the proper focus distance to either the calibration ball 70 or to the tested surface 28 to ensure applicability of the calibration to the specific test surface evaluation.

FIG. 9 illustrates schematically one embodiment of the focus alignment sensing device 51, i.e. a telemicroscope, integrated into the corneal topography measuring apparatus 35. In this embodiment, means are provided for the user's eye 53 to observe a view along the axis 27 of the reflected pattern of LED images from surface 28' via beamsplitter 52, lens 54, mirror 55A, and eyepiece 56 (see FIG. 9). Alignment reference is achieved by internal means such as a cross-hair reticle pattern 57 located at the image of the LED pattern. In use during calibration, this optical subsystem allows the surface 28' to be centered vertically and horizontally through action of adjustable fixture 36. In use during measurement of a cornea, this subsystem provides a reference for vertical and horizontal alignment of the vertex of the eye through action of appropriate mechanisms which adjust position of the subject's head and/or eye.

Another feature of the apparatus shown in FIG. 9 is the alternate telemicroscope path formed by movement of mirror 55A out of the above-described optical path to a position such as is shown at 55B. An image of a side view of surface 28' or of the surface under test will then be accessed by means of mirror 58 and lens 59 used in conjunction with the remaining components of the basic telemicroscope. The appearance of the field of view of said adapted telemicroscope in the focus measurement mode during calibration is illustrated schematically in FIG. 10. A similar view showing proper alignment of the eye cornea to the telemicroscope's crosshair pattern is shown in FIG. 11. It should be noted that it is preferable, but not essential, that the image presented to the operator's eye be erect since this would facilitate use of the device.

FIG. 12 represents one embodiment of an image-erecting focus alignment measuring telemicroscope means 60 incorporated by mechanical structure, not shown, into a laser sculpturing apparatus 61 which is equipped with a corneal topography measuring apparatus of the type described herein.

The main requirements of the disclosed topography measuring device are the acquisition of video images and the processing of the captured images according to a fixed algorithm. Conventional frame grabbers, such as the frame grabber 23 illustrated in FIG. 1, not only acquire captured images as required by the present invention, but also perform unnecessary functions such as look-up tables, video mixes, and video reconstruction digital to analog. A conventional personal computer or its equivalent, provides an adequate environment for most software tasks. However, it is ill equipped to process video images with any significant speed.

An alternative for frame grabber 23 is a frame grabber stripped of all unneeded features and only equipped with a powerful microprocessor dedicated to the data reduction algorithm. Conventional microprocessors of this type, such as digital signal processors, offer a speed advantage which is at least a factor of 10 more than the conventional frame grabbers disclosed herein. The circuit board design which would be located in a conventional PC, consists of a video digitizer, memory banks to store the video images, a digital signal processor, and the necessary circuitry to interface with the PC.

The design of the topography measuring device described hereinbefore has two areas which are thought to be subject to improvement. These are (1) the ability to achieve high accuracy in centering the alignment of an eye in the transverse directions, i.e. perpendicular to the optical axis through the topography measuring apparatus (also called a digital keratoscope); and (2) the ability to provide information about the corneal topography close to the optical axis.

The current techniques for determining adequacy of centering alignment of the eye are (1) operator judgment of the symmetry of the individual images and of the array of images reflected from the cornea as seen on the video monitor or (2) centering the visual image of the patient's iris or limbus on some markings on the device used to fixate the eye during surgery as seen through a coaxial optical microscope. Since there is no clearly distinguishable feature in these observables which indicates the precise location of the axis of the cornea to be matched to a crosshair reticle pattern in the microscope, alignment is only approximate.

Figure 13:
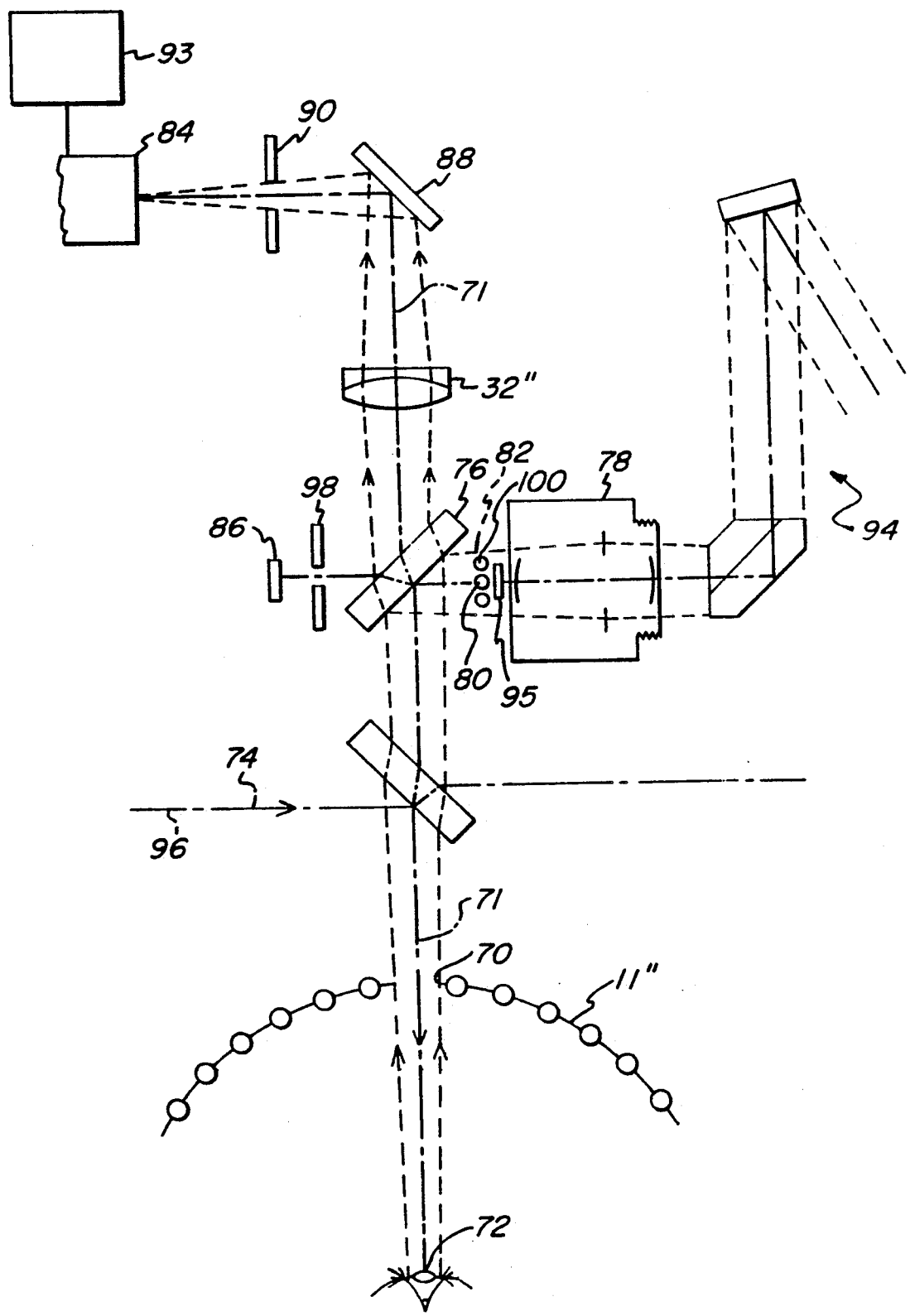
FIG. 13 is a simplified diagram relating a second embodiment of the alignment mechanism to align the eye with the laser sculpting apparatus.

Although the invention illustrated in FIG. 13 is particularly described in conjunction with measuring the cornea of an eye, it is within the terms of the present invention to use it for measuring any surface and, in particular, any substantially spherical surface.

To correct these deficiencies, eye centering alignment can be facilitated by installing a point light source, such as a LED or an equivalent light source, on or substantially on, e.g. appearing to be on, the axis of the digital keratometer. The image of this light source, as reflected from the cornea, would only appear on the video monitor to lie on the digital keratometer axis if the center of curvature of the cornea lies on the digital keratometer axis. This principle is conventionally used in aligning optical surfaces, such as lenses or mirrors, to the axis of optical instruments.

Referring to FIG. 13, the curved source array 11'', preferably comprising a nominally or substantially spherical surface, has a hole or aperture 70 located in the middle of the array, concentric with the axis 71 through the digital keratomer. Since elements of the cornea measuring devices disclosed herein can be substantially identical, primed and double primed numbers are used to indicate like elements. The aperture 70 enables both the reflected beams from the cornea 72 to reflect to an imaging lens 32″ while the UV laser beam 74 is simultaneously projected coaxially onto the cornea 72. In order for an on-axis light source to be projected onto the cornea 72, it must be introduced by a conventional beam splitter or beamcombining device 76. The beamcombining device is positioned in front of the visual microscope objective 78. If a LED or other type of conventional point light source 80 is located on a folded optical axis 82, disposed transverse to the optical axis 71 through the system, between the beamsplitter 76 and the microscope objective 78, light from source 80 will reflect from the beamsplitter in a downward direction along axis 71 to the cornea 72 and will then serve as the on-axis point source for eye centering alignment purposes.

A reference against which to judge centering alignment of the eye could be a crosshair or other suitable pattern electronically superimposed on the video image formed in video camera 84 by conventional means, such as cross hair 57 illustrated in FIG. 9.

In alternative embodiments, some light from the on-axis source 80 passing directly through the beamsplitter 76 could fall upon an adjustable and lockable mirror 86. Mirror 86 would reflect a portion of the light from source 80 upward from the beamsplitter 76 through the imaging lens 32″ off mirror 88, through the aperture stop 90 so as to form an image of the source 80 on the video camera 84. This image of source 80 would then serve as a fixed reference of the optical axis 71 through the digital keratometer since its location is not affected by the centering of the cornea 72. Although an adjustable and lockable mirror 86 is illustrated, it is within the terms of the present invention to substitute any equivalent retrodirective device such as a cube corner prism or a "cats-eye reflector". The latter equivalent structures are advantageous, as compared to the adjustable and lockable mirror, since a fixed position device would be retrodirective and less sensitive to its own misalignment in the system.

Figure 14:
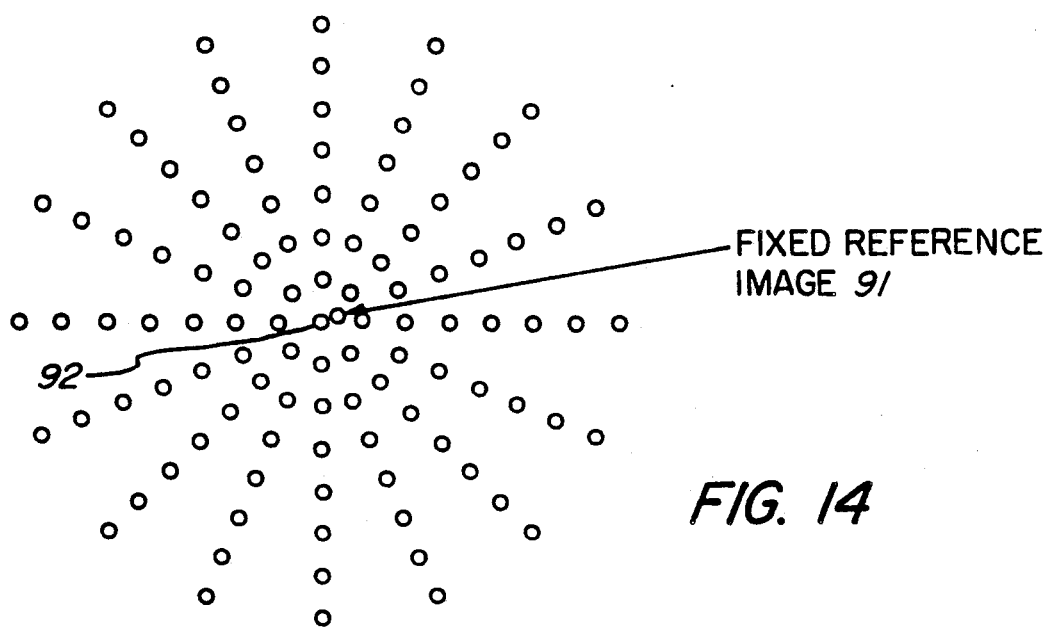
FIG. 14 is a diagram of the image formed on a video camera through use of apparatus illustrated in FIG. 13.

The image formed on the video camera 84 would typically appear as shown in FIG. 14. The location of the reference image 92, corresponding to the location of the axis through the contour measuring apparatus, can then be compared with the location of the center of the cornea being measured. For clarity, the image in FIG. 14 corresponds to a slightly decentered cornea so the LED images reflected from that cornea appear proportionately decentered with respect to the fixed central source reference image 91. In use, when such a decentered pattern is observed, the cornea is preferably moved laterally until the image 92 corresponding to the central source 80 as seen reflected from the cornea 72, is superimposed upon the reference image 91 of that same source 80 seen by way of reflection from the adjustable and lockable mirror element 86.

It should be noted that the optical magnification and luminance of the two images of the central source 80 should be essentially the same so that those images appear to be approximately the same size and intensity in the composite image presented on a video monitor 93 connected to video camera 84. This can be accomplished by conventional means, such as selecting the effective relative apertures and light transmissions of the optics in the beams forming the two images to be essentially the same or by appropriately compensating therefor.

A conventional visual microscope 94 is provided on the folded optical axis 82 for observing the surface 72 being measured. This enables an operator to initially align the contour measuring apparatus or to observe the cornea or other surface being measured.

A light shield 95 can be disposed between the point light source 80 and the visual microscope 94 to prevent light from the point light source 80 from entering the microscope 94 and reduce the clarity with which the surface being measured can be observed.

As discussed hereinbefore, the focusing device 90, comprising an aperture stop or any such equivalent structure limits the cone angle of the rays of the first light beams reflected from the surface 72 whereby each of the reflected rays closely approximates a telecentric principal ray corresponding to a light point on the multi-point light source 11″.

As described hereinbefore, the contour measuring apparatus is particularly adapted for use with a laser sculpturing apparatus having an axis 96 of sculpturing laser beam 74 delivery in coincidence with the optical axis 71 of the contour measuring apparatus. The laser sculpturing apparatus can be interconnected with the contour measuring apparatus for combined laser sculpturing and cornea evaluation operations.

As described hereinbefore, a signal switch, a frame grabber and a computer, as illustrated in FIG. 1, can be in electrical communication with the photodetector in video camera 84 for determining both the local radius of curvature of the surface 72 at each desired point of incidence of the individual light beams and the three-dimensional contours of the surface.

In another embodiment, additional point light sources 100 can be located around the central reference source 80 to provide additional corneal topography measurement capability near the central axis through the corneal surface of the eye. It can be understood that the need for an aperture 70 in light source 11″, to enable light reflections from surface 72 to be directed along axis 71, provides a structural limitation as to positioning light sources close to axis 71. Thus, the light points 100 can be directed through the aperture 70 to reflect off the surface 72 at a position very near the central axis through surface 72. For this embodiment to be most effective, the central single source can initially be utilized as described before to center the eye. Then, the light from source 80 forming the fixed central reference image can be obscured by any conventional means such as closing shutter device 98 located between the beamsplitter 76 and the reflecting means 86. By obscuring the light with shutter 98, only the images reflected from the cornea are used to measure topography. This design feature allows measurement to within about 0.25 mm from the axis 71.

Figure 15:
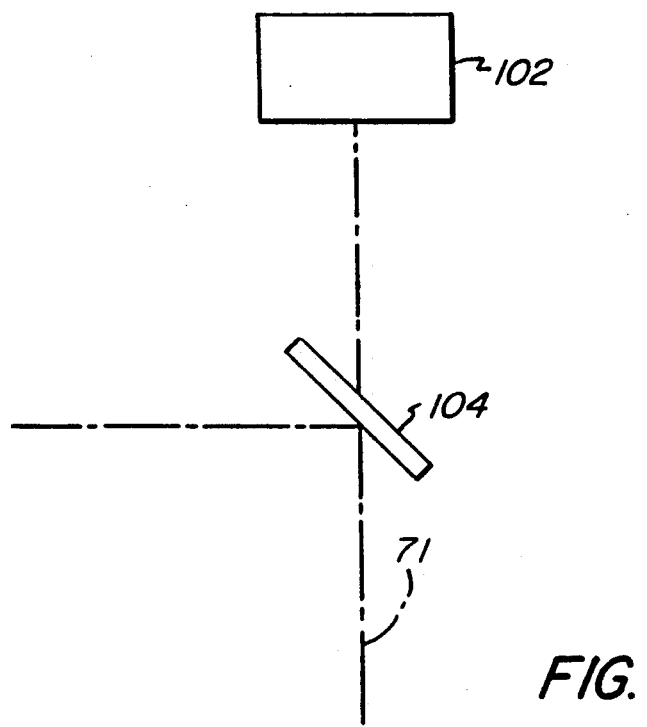
FIG. 15 is a diagram showing a CCD array on an image plane.

In a further embodiment, as illustrated in FIG. 15, the detected signals 91 and 92 corresponding to the fixed reference, i.e. axis 71, and the center of surface 72, can be generated by a separate electro-optical sensor system 102 which only receives the light rays from the central images during a laser sculpting surgical procedure. The light rays are provided through a narrow light path in a beam splitter 104 which is substituted for the beam splitter 88 of FIG. 13.

An advantage of this embodiment is that the light source 80 can monitor motion of the eye that could degrade the surgical results. The photosensor 102, by only monitoring the dual central images 91 and 92, could provide an error signal whenever the two images were not superimposed within some acceptable tolerance. Sensor 102 could, for example, monitor the apparent diameters of the dual images in several directions and provide an error signal in response to broadening of the image in some direction due to misalignment of the cornea with the optical axis through the contour measuring apparatus. The error signal could function to alert the operator to turn off the laser beam or to drive a servo-controlled eye positioning system to maintain proper alignment of the eye in the apparatus during the surgical procedure. For example, an apparatus such as alignment apparatus 36, as illustrated in FIG. 4A, could be used to electro-mechanically control the alignment of eye 72 in conjunction with the error signal generated by sensor 102. It is also within the terms of the present invention to monitor the detected signals 91 and 92 with the video processing equipment used to process the optical images reflected onto video camera 84. The processing equipment could be programmed to isolate the detected signals 91 and 92 and provide an error signal as described hereinbefore.

In addition to providing the above described advantages, the beam from the central light source 80, which is reflected from the beamsplitter 76 towards the cornea 72, could be used as a fixation target for sighted eyes being examined in the digital keratoscope as a stand-alone diagnostic instrument. This source would be on the axis 82 and would cause the visual axis of the eye to coincide with axis 71.

While the present invention has been described primarily for use in measuring the contour of a cornea, it can also be used to measure the shape of any regular or irregular contoured surface. For example, the invention could be used to measure the contour of optical lenses, mirrors, ball bearings and precision machine parts, to name a few.

The patents and patent applications set forth in this application are intended to be incorporated by reference herein.

It is apparent that there has been provided in accordance with this invention a method and apparatus for measuring the topography of a contoured surface which satisfies the objects, means, and advantages set forth hereinabove. While the invention has been described in combination with the embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A contour measuring apparatus to measure the three-dimensional contour of a surface, comprising:
    means to direct first light beams onto the surface being measured;
    means receiving reflections of the first light beams from said surface for generating electrical output signals corresponding to electro-optically measurable optical images, each of said images corresponding to the location of said first light beams; and
    means for determining the location of the center of the surface being measured with respect to an optical axis extending through the contour measuring apparatus, the location determining means comprising:
        means for directing a single light beam along the optical axis of said contour measuring apparatus onto the surface being measured so as to reflect to the means for generating electrical output signals;
        means for generating a pattern in said means for generating electrical output signals corresponding to the location of the optical axis through the contour measuring apparatus; and
        means to compare the location of the center of the surface being measured with the location of the optical axis.

2. The contour measuring apparatus of claim 1 wherein said means to direct a single light beam comprises:
    a single point light source located on a folded optical axis disposed transverse to said optical axis; and
    a beam splitter on the optical axis in front of the single point light source to reflect the single light beam from the single point light source in the direction of the surface being measured to indicate the location of the center of the surface being measured.

3. The contour measuring apparatus of claim 2 wherein said single point light source comprises a LED.

4. The contour measuring apparatus of claim 2 further comprising a visual microscope on the folded optical axis for observing the surface being measured and the reflections therefrom of the first light beams and of the single light source.

5. The contour measuring apparatus of claim 4 further comprising a light shield between said point light source and said visual microscope to prevent light from said point light source from entering directly into said microscope.

6. The contour measuring apparatus of claim 2 further comprising reflector means on the folded optical axis opposite said beam splitter from the point light source for returning a portion of the light from the point light source to the reflections receiving means to serve as a fixed reference of the location of the optical axis through the contour measuring apparatus.

7. The contour measuring apparatus of claim 6 wherein said reflector means comprises an adjustable and lockable mirror.

8. The contour measuring apparatus of claim 6 wherein said reflecting means comprises a retrodirective device such as a cube corner prism.

9. The contour measuring apparatus of claim 6 wherein said reflector means comprises a cats-eye reflector.

10. The contour measuring apparatus of claim 2 further comprising an electronically superimposed pattern in said means receiving reflections corresponding to the location of the optical axis through said contour measuring apparatus.

11. The contour measuring apparatus of claim 2 further comprising means disposed between said surface being measured and said means for generating electrical output signals for focusing the reflected first light beams and the reflected single beam of light from the surface being measured onto the means for receiving reflections.

12. The contour measuring apparatus of claim 11 wherein
   the focusing means comprises a lens having said optical axis extending therethrough; and
   said means for receiving reflections comprises a photodetector.

13. The contour measuring apparatus of claim 12 wherein said means to direct first light beams comprises a multi-point light source for directing a plurality of individual light beams each corresponding to individual light points of the multi-point light source onto the surface being measured.

14. The contour measuring apparatus of claim 13 further including means between the focusing means and said photodetector for limiting the cone angle of the rays of said first light beams reflected from the surface whereby each of the reflected rays closely approximates a telecentric principal ray corresponding to a single light point of the multi-point light source.

15. The contour measuring apparatus of claim 1 wherein said means to direct first light beams comprises a multi-point light source for directing a plurality of individual light beams each corresponding to individual light points of the multi-point light source onto the surface being measured.

16. The contour measuring apparatus of claim 2 wherein said means for generating electrical output signals includes:
   a video camera producing an image of the surface being measured; and
   a monitor connected to said video camera receiving said image for observation by the operator.

17. The contour measuring apparatus of claim 1 wherein the surface being measured is substantially spherical.

18. The contour measuring apparatus of claim 17 wherein the substantially spherical surface is the anterior surface of a cornea.

19. The contour measuring apparatus of claim 18 including:
   laser-sculpturing apparatus having an axis of sculpturing laser beam delivery in coincidence with the optical axis of the contour measuring apparatus; and
   means interconnecting said laser-sculpturing apparatus and said contour measuring apparatus for combined individual laser sculpturing and corneal contour evaluation operations.

20. The contour measuring apparatus of claim 6 wherein the means to direct first light beams comprises a nominally spherical surface having its center on the optical axis of the measuring apparatus.

21. The contour measuring apparatus of claim 2 including one or more point light sources disposed adjacent the folded optical axis adapted to be reflected from the beam splitter onto the optical axis in the direction of the surface being measured to enable the determination of the local radius of curvature of the measured surface near the optical axis.

22. The contour measuring apparatus of claim 1 wherein the means to direct first light beams comprises a surface having an aperture centered on the optical axis of the system to enable light beams to be reflected from the surface being measured to the means for generating electrical output signals.

23. The contour measuring apparatus of claim 22 wherein the measurement of the contour of the surface being measured can be made within about 0.25 mm of the optical axis.

24. The contour measuring apparatus of claim 6 including one or more point light sources disposed adjacent to the folded optical axis adapted to be reflected off of the beam splitter on the optical axis in the direction of the surface being measured to enable the determination of the local radius of curvature of the measured surface near the optical axis.

25. The contour measuring apparatus of claim 24 wherein the means to direct first light beams comprises a substantially spherical surface having its center on the optical axis of the measuring apparatus.

26. The contour measuring apparatus of claim 20 wherein said spherical surface includes an aperture centered on the optical axis of the system to enable light beams to be reflected from the surface being measured to the means for generating electrical output signals

27. The contour measuring apparatus of claim 26 further including
   means disposed between the reflector means and the single point light source to prevent light originating in the single point light source and reflected from the beam reflector to the reflection receiving means from generating a pattern corresponding to the location of the optical axis in the electrical output signals generating means; and
   means receiving said electrical output signals from said means for measuring the position of the optical images reflected from the surface being measured and for determining the local radius of curvature of the measured surface.

28. The contour measuring apparatus of claim 27 wherein the measurement of the curvature of the surface being measured can be made within about 0.25 mm of the optical axis.

29. The contour measuring apparatus of claim 1 further comprising:
   means for selectively monitoring the dual image corresponding to the position of the center of the surface being measured and the optical axis through the contour measuring apparatus; and
   means for generating an error signal in response to broadening of the dual image due to misalignment of the center of the surface being measured with the optical axis through the contour measuring apparatus.

30. The contour measuring apparatus of claim 29 further including a servo-controlled positioning system to maintain alignment of the center of the surface being measured with respect to the optical axis through the apparatus.

31. The method of measuring the three-dimensional contour of a surface with a contour measuring apparatus comprising the steps of:
   directing first light beams onto the surface being measured;
   receiving reflections of the first light beams from said surface for generating electrical output signals corresponding to electro-optically measurable optical images, each of said images corresponding to the location of said first light beams; and
   determining the location of the center of the surface being measured with respect to an optical axis extending through the contour measuring apparatus, the location determining step comprising the steps of:

directing a single light beam along the optical axis to reflect from the surface being measured so as to generate electrical output signals corresponding to the center of the measured surface;

generating a pattern of the electrical output signals corresponding to the location of the optical axis through the contour measuring apparatus; and comparing the approximate location of the center of the surface being measured with the location of the optical axis.

32. The method of claim 31 wherein the steps of directing a single light beam comprises:

locating a single point light source on a folded optical axis disposed transverse to said optical axis; and disposing a beam splitter on the optical axis in front of the single point light source to reflect the single light beam in the direction of the surface being measured to indicate the location of the center of the surface being measured.

33. The method of claim 32 including the step of observing the surface being measured through a visual microscope disposed on the folded optical axis.

34. The method of claim 33 including the step of preventing light from said point light source from entering directly into said microscope.

35. The method of claim 32 including the step of reflecting a portion of the light from the point light source to generate a pattern of electrical output signals which serve as a fixed reference of the location of the optical axis through the contour measuring apparatus.

36. The method of claim 35 further comprising the step of focusing the reflected first light beams and single beam of light from the surface being measured for generating electrical output signals.

37. The method of claim 36 further including the step of limiting the cone angle of the rays of said first light beams reflected from the surface whereby each of the reflected rays closely approximates a telecentric principal ray corresponding to a light point.

38. The method of claim 31 wherein the surface being measured is the substantially spherical anterior surface of a cornea.

39. The method of claim 38 including the steps of:

providing laser-sculpturing apparatus having an axis of sculpturing laser beam delivery in coincidence with the optical axis of the contour measuring apparatus; and interconnecting said laser-sculpturing apparatus and said contour measuring apparatus for combined individual laser sculpturing and cornea evaluation operations.

40. The method of claim 32 including the step of disposing one or more point light sources adjacent the folded optical axis to reflect from the beam splitter on to the optical axis in the direction of the surface being measured to enable the determination of the local radius of curvature of the measured surface near the optical axis.

41. The method of claim 31 including the step of measuring the curvature of the surface being measured within about 0.25 mm of the optical axis.

42. The method of claim 31 further including the steps of:

selectively monitoring the dual image corresponding to the position of the center of the surface being measured and the optical axis through the contour measuring apparatus; and generating an error signal in response to broadening of the dual image due to misalignment of the center of the surface being measured with the optical axis through the contour measuring apparatus.

* * * * *